United States Patent
de Villers-Sidani et al.

(10) Patent No.: US 11,139,066 B2
(45) Date of Patent: *Oct. 5, 2021

(54) METHOD OF SUPPRESSING OF IRRELEVANT STIMULI

(71) Applicant: The Regents of the University of California, Oakland, CA (US)

(72) Inventors: Etienne de Villers-Sidani, Montreal (CA); Xiaoming Zhou, San Francisco, CA (US); Jyoti Mishra-Ramanathan, San Francisco, CA (US); Michael Merzenich, San Francisco, CA (US); Adam Gazzaley, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/888,358

(22) Filed: May 29, 2020

(65) Prior Publication Data

US 2020/0365051 A1    Nov. 19, 2020

Related U.S. Application Data

(63) Continuation of application No. 13/704,922, filed as application No. PCT/US2011/041504 on Jun. 22, 2011, now Pat. No. 10,672,292.

(Continued)

(51) Int. Cl.
*A61B 5/378*    (2021.01)
*G09B 19/00*    (2006.01)
(Continued)

(52) U.S. Cl.
CPC ............ *G16H 20/70* (2018.01); *A61B 5/378* (2021.01); *G09B 19/00* (2013.01); *G16H 20/30* (2018.01); *Y02A 90/10* (2018.01)

(58) Field of Classification Search
CPC ... A61B 5/4088; A61B 5/4082; A61B 5/4076; A61B 5/38; A61B 5/378; A61B 5/377; G09B 19/00; G09B 7/00; G09B 7/02
See application file for complete search history.

(56) References Cited

U.S. PATENT DOCUMENTS 5,137,027 A    8/1992    Rosenfeld
5,303,327 A    4/1994    Sturner et al.
(Continued)

FOREIGN PATENT DOCUMENTS

JP    200513713    1/2005
JP    2007292908   11/2007
(Continued)

OTHER PUBLICATIONS

Anguera et al. (2010) "Age-Related Changes in Distraction & Multitasking during a Driving Video Game" Department of Neurology and Physiology, W.M. Keck Center for Integrative Neurosciences, University of California San Francisco, San Francisco, California. Nov. 16, 2010. Poster.
(Continued)

*Primary Examiner* — Robert J Utama
(74) *Attorney, Agent, or Firm* — Brian E. Davy; Bozicevic, Field & Francis LLP

(57) ABSTRACT

The present disclosure relates to methods and tools for enhancing cognition in an individual. The methods involve presenting to the individual multiple sets of stimuli. Each set of the multiple set contains two or more stimuli and at least one set of the multiple sets contains a target stimulus. The method then receives an input from the individual, and informs the individual as to whether the input is a correct response. The methods encompass iterations of stimuli presentation, receiving of the input, and lastly, generation of feedback to the individual until the individual learns and retains what the target stimulus is.

20 Claims, 3 Drawing Sheets

Related U.S. Application Data

(60) Provisional application No. 61/359,290, filed on Jun. 28, 2010.

(51) Int. Cl.
    *G16H 20/70*         (2018.01)
    *G16H 20/30*         (2018.01)

(56) References Cited

U.S. PATENT DOCUMENTS

| | | |
|---|---|---|
| 5,363,858 A | 11/1994 | Farwell |
| 5,762,611 A | 6/1998 | Lewis et al. |
| 6,261,101 B1 | 7/2001 | Benitz et al. |
| 6,290,504 B1 | 9/2001 | Benitz et al. |
| 6,413,098 B1 | 7/2002 | Tallel et al. |
| 6,549,752 B2 | 4/2003 | Tsukamoto |
| 6,632,174 B1 | 10/2003 | Breznitz |
| 6,746,409 B2 | 6/2004 | Keirsbilck et al. |
| 6,832,110 B2 | 12/2004 | Sohmer et al. |
| 6,840,908 B2 | 1/2005 | Edwards et al. |
| 7,384,399 B2 | 6/2008 | Ghajar |
| 7,540,615 B2 | 6/2009 | Merzenich et al. |
| 7,774,052 B2 | 8/2010 | Burton et al. |
| 8,231,543 B2 | 7/2012 | Benasich et al. |
| 8,951,206 B2 | 2/2015 | Benasich et al. |
| 2004/0037236 A1 | 2/2004 | Massey et al. |
| 2004/0049124 A1 | 3/2004 | Kullok et al. |
| 2005/0273017 A1 | 12/2005 | Gordon |
| 2005/0283053 A1 | 12/2005 | deCharms |
| 2006/0073452 A1 | 4/2006 | Goldman et al. |
| 2006/0252014 A1 | 11/2006 | Simon et al. |
| 2006/0292531 A1 | 12/2006 | Gibson |
| 2007/0009864 A1 | 1/2007 | Rikimaru et al. |
| 2007/0031798 A1 | 2/2007 | Gottfried |
| 2007/0134635 A1 | 6/2007 | Hardy et al. |
| 2007/0141541 A1 | 6/2007 | Chan et al. |
| 2007/0166675 A1 | 7/2007 | Atkins et al. |
| 2007/0191727 A1 | 8/2007 | Fadem |
| 2007/0218440 A1 | 9/2007 | Delahunt et al. |
| 2007/0293735 A1 | 12/2007 | Chan et al. |
| 2007/0299319 A1 | 12/2007 | Chan et al. |
| 2008/0003558 A1 | 1/2008 | Chan et al. |
| 2009/0005648 A1 | 1/2009 | Teicher et al. |
| 2009/0306534 A1 | 12/2009 | Pizzagalli |
| 2009/0312817 A1 | 12/2009 | Hogle et al. |
| 2009/0319380 A1 | 12/2009 | Jacoby et al. |
| 2010/0041001 A1 | 2/2010 | Delahunt et al. |
| 2010/0092929 A1* | 4/2010 | Hallowell ............... A61B 3/113 434/167 |
| 2010/0094162 A1 | 4/2010 | Benasich et al. |
| 2010/0249532 A1 | 9/2010 | Maddess et al. |
| 2013/0203027 A1 | 8/2013 | de Villers-Sidani et al. |
| 2013/0216985 A1 | 8/2013 | de Villers-Sidani et al. |
| 2014/0148728 A1 | 5/2014 | Eizenman et al. |
| 2014/0370479 A1 | 12/2014 | Gazzaley |
| 2016/0117940 A1 | 4/2016 | Gomory et al. |
| 2016/0267804 A1 | 9/2016 | Pemba et al. |

FOREIGN PATENT DOCUMENTS

| | | |
|---|---|---|
| JP | 2009237104 | 10/2009 |
| WO | WO 2007070876 | 6/2007 |
| WO | WO 2008013907 | 1/2008 |

OTHER PUBLICATIONS

Adolfsdottir et al. (2008) "The attention network test: a characteristic pattern of deficits in children with ADHD", Behavioral and Brain Functions, 4(9).

Anguera et al. (2010) "Age-Related Changes in Distraction & Multitasking during a Driving Video Game" Department of Neurology and Physiology, W.M. Keck Center for Integrative Neurosciences, University of California San Francisco, San Francisco, California. Nov. 3, 2010. Abstract.

Berry et al. (2009) "Practice-Related Improvement in Working Memory is Modulated by Changes in Processing External Interference" *J Neurophysiol* 102:1779-1789.

Bherer et al. (2008) "Transfer effects in task-set cost and dual-task cost after dual-task training in older and younger adults: further evidence for cognitive plasticity in attentional control in late adulthood" *Exp Aging Res* 34(3):188-219.

Blake & Merzenich (2002) "Changes of AI receptive fields with sound density" *J Neurophysiol* 88(6):3409-3420.

Blake et al. (2002) "Sensory representation abnormalities that parallel focal hand dystonia in a primate model" *Somatosens Mot Res* 19(4):347-357.

Carry the One Radio Interview with Adam Gazzaley Jan. 15, 2010. Transcript. http://www.carrytheoneradio.com/2010/01/20/adam-gazzaley/.

Chao & Knight (1997) "Prefrontal deficits in attention and inhibitory control with aging" *Cereb Cortex* 7:63-69.

Clapp & Gazzaley (2012) "Distinct mechanisms for the impact of distraction and interruption on working memory in aging" *Neurobiol Aging* 33(1): 134-148. doi: 10.1016/j.neurobiolaging.2010.01.012. Epub Feb. 9, 2010.

Clapp et al. (2009) "Mechanisms of working memory disruption by external interference" *Cereb Cortex* 20:859-872.

Czigler et al. (1992) "Age and Inter-Stimulus Interval Effects on Event-Related Potentials to Frequent and Infrequent Auditory Stimuli" *Biol Psychol* 33(2-3):195-206.

Dahlin et al. (2008) "Transfer of learning after updating training mediated by the striatum", Science, 320(5882): 1510-1512.

De Villers-Sidani et al. (2010) "Recovery of Functional and Structural Age-Related Changes in the Rat Primary Auditory Cortex with Operant Training" *Proc Natl Acad Sci* USA 107(31):13900-13905.

Decharms et al. (1998) "Optimizing sound features for cortical neurons" *Science* 280(5368):1439-1443.

Draganova et al. (2009) "Modulation of Auditory Evoked Responses to Spectral and Temporal Changes by Behavioral Discrimination Training" *BMC Neurosci* 143. doi: 10.1186/1471-2202-10-143.

Duncan-Johnson & Donchin (1977) "On Quantifying Surprise: The Variation of Event-Related Potentials with Subjective Probability" *Psychophysiology* 14(5):456-467.

Endsley et al. "Disruptions, interruptions and information attack: Impact on sitution awareness and decision making" Clara, CA: SA Technologies, Inc; 2001.

Eriksen & Eriksen (1974) "Effects of noise letters upon the identification of a target letter in a nonsearch task", Perception and Psychophysics, 16:143-149.

Fan et al. (2002) "Testing the efficiency and independence of attentional networks", J Cogn Neurosci., 14(3):340-7.

Gazzaley et al. (2005) "Top-down suppression deficit underlies working memory impairment in normal aging" *Nat Neurosci* 8(10):1298-1300.

Greenberg & Waldman (1993) "Developmental normative data on the test of variables of attention (T.O.V.A.)" *J Child Psychol Psychiatry* 34(6):1019-1030.

Hasher et al. (1991) "Age and inhibition" *J Exp Psychol Learn Mem Cogn* 17(1):163-169.

Herrmann & Knight (2001) "Mechanisms of Human Attention: Event-Related Potentials and Oscillations" *Neurosci Biobehav Rev* 25(6):465-476.

Jaeggi et al. (2008) "Improving fluid intelligence with training on working.memory", Proc Natl Acad Sci USA, 105:6829-6833.

Jeon & Polich (2003) "Meta-Analysis of P300 and Schizophrenia: Patients, Paradigms, and Practical Implications" *Psychophysiology* 40(5):684-701.

Kelland & Lewis (1996) "The Digit Vigilance Test: reliability, validity, and sensitivity to diazepam" *Arch Clin Neuropsychol* 11(4):339-344.

Kelly & Yantis (2009) "Learning to attend: Effects of practice on information selection", Journal of Vision, 9(7): 1-18.

Kilgard & Merzenich (1998) "Cortical map reorganization enabled by nucleus basalis activity" *Science* 279(5357):1714-1718.

Klingberg et al. (2002) "Training of Working Memory in Children with ADHD", Journal of Clinical and Experimental Neuropsychology, 24(6):781-791.

(56) References Cited

OTHER PUBLICATIONS

Klingberg et al. (2005) "Computerized training of working memory in children with ADHD-a randomized, controlled trial", Journal of the American Academy of Child and Adolescent Psychiatry, 44(2):177-186.
Klingberg (2010) "Training and plasticity of working memory", Trends in Cognitive Sciences, 14:317-324.
Lustig et al. (2009) Aging, training, and the brain: a review and future directions, Neuropsychological Review, 19: 504-522.
Machado et al. (2009) "Distractibility with advancing age and Parkinson's disease", Neuropsychologia, 47(7):1756-64.
McIlroy "Does Play Really Keep Dementia at Bay?" *Globe and Mail* Sep. 22, 2010.
Morrison et al. (2011) "Does working memory training work? The promise and challenges of enhancing cognition by training working memory", Psychonomic Bulletin Review, 18:46-60.
Ophir et al. (2009) "Cognitive control in media multitaskers" *Proc Natl Acad Sci USA* 106(37):15583-15587.
Olesen et al. (2004) "Increased prefrontal and parietal brain activity after training of working memory", Nature Neuroscience, 7(1):75-79.
Olson & Jiang (2004) "Visual short-term memory is not improved by training", Memory & cognition, 32(8): 1326-1332.
Owen et al., (2010) "Putting brain training to the test", Nature, 465:775-778.
Persson & Reuter-Lorenz (2008) "Gaining control: training executive function and far transfer of the ability to resolve interference", Psychological Science, 19(9):881-8.
Polley et al. (2006) "Perceptual learning directs auditory cortical map reorganization through top-down influences" *J Neurosci* 26(18):4970-4982.
Rasmusson et al. (1995) "Stability of performance on the Hopkins Verbal Learning Test" *Arch Clin Neuropsychol* 10(1):21-26.
Robertson & Irvine (1989) "Plasticity of frequency organization in auditory cortex of guinea pigs with partial unilateral deafness" *J Comp Neurol* 282(3):456-471.
Robertson et al. (1997) "'Oops!': performance correlates of everyday attentional failures in traumatic brain injured and normal subjects" *Neuropsychologia* 35(6):747-758.
Royan et al. (2004) "The Adjusting-Paced Serial Addition Test (Adjusting-PSAT): thresholds for speed of information processing as a function of stimulus modality and problem complexity" *Arch Clin Neuropsychol* 19(1):131-143.
Rutkowski et al. (2005) "Encoding of learned importance of sound by magnitude of representational area in primary auditory cortex" *Proc Natl Acad Sci USA* 102(38):13664-13669.
Shiffrin et al. "Controlled and Automatic Human Information Processing:" vol. 84, No. 2, Mar. 1977.
Shipstead et al. (2010) "Does working memory training generalize?", Psychologica Belgica, 50:245-276.
Siu et al. (2008) "Does inability to allocate attention contribute to balance constraints during gait in older adults?" *J Gerontol A Biol Sci Med Sci* 63(12):1364-1369.
Smith et al. (2009) "A cognitive training program based on principles of brain plasticity: results from the Improvement in Memory with Plasticity-based Adaptive Cognitive Training (IMPACT) study" *J Am Geriatric Soc* 57(4):594-603.
Stuss et al. (1987) "Comparison of three tests of attention and rapid information processing across six age groups" *Clinical Neuropsychologist* 1(2):139-152.
Third Party Observations, EP11840579.4, (2017), 227 pages.
Ulanovsky et al. (2003) "Processing of low-probability sounds by cortical neurons" *Nat Neurosci* 6(4):391-398.
Van Rossum (2001) "A novel spike distance" *Neural Comput* 13(4):751-763.
Wilson (2003) "Development of a speech-in-multitalker-babble paradigm to assess word-recognition performance" *J Am Acad Audiol* 14(9):453-470.
Zhang et al. (2001) "Persistent and specific influences of early acoustic environments on primary auditory cortex" *Nat Neurosci* 4(11):1123-1130.

* cited by examiner

*A)*

*B)* Performance Improvement in Irrelevant Stimulus Suppression Training

*C)* Performance Variance in Irrelevant Stimulus Suppression Training

D)

METHOD OF SUPPRESSING OF IRRELEVANT STIMULI

CROSS-REFERENCE TO RELATED APPLICATIONS

This application is a continuation of Ser. No. 13/704,922 filed Apr. 26, 2013, which is a 371 National Phase of International Patent Application Serial No. PCT/US2011/041504 filed Jun. 22, 2011, which claims the benefit of U.S. Provisional application Ser. No. 61/359,290, filed on Jun. 28, 2010, which application is incorporated herein by reference in its entirety.

INTRODUCTION

Perceptual and cognitive decline are near-universal aspects of normal aging. Such deficits cannot be explained solely by a dysfunction of peripheral sensory organs and frequently translate to slowed perceptual processing and difficulty in accurately identifying stimuli under challenging (noisy, time-limited, attentionally-demanding) conditions.

One linchpin deficit that distinguishes the old from the young brain is the deterioration of the neurological processes that normally suppress ('adapt to') those unchanging backgrounds. Because the brain does not adapt to (e.g. reduces its responses to) constant or identically-repeated background stimuli, its ongoing neurological activities are far noisier, and old rats continued to make many more erroneous ('false positive') behavioral responses than did young rats.

In studies of attentional control in the adult brain, two great processes are in play. First, the cortex is activated selectively (humans 'selectively attend' to specific stimulus events) as the focus is shifted to different specific features within the behavioral landscape. This selective activation is paralleled by signature ('activating') changes in brain wave activity. Selective attention results in a sharp amplification of the responses to any stimulus that is being specifically attended to.

Second, the young cortex very effectively suppresses all other (not-selectively-attended) stimuli. Again, this 'active ignoring' of non-attended stimuli is manifested by signature ('suppressing') changes in brain wave activity. In the common vernacular, the healthy cortex activates the cortex that represents what it is selectively attending to, and simultaneously, sharply attenuates its responses to any stimulus that could distract the individual from that selective attending. The relatively weak suppression of repeated background stimuli found in old rats provides evidence that the old rat brain is doing a poor job of 'active ignoring' (suppressing background stimuli). Older humans are similarly poor suppressors. As a result, they are hyper-sensitive to distracting stimuli, have behaviors marked by many more erroneous ('false-positive') responses, and are very impaired in their suppression of repeated or constant (for signal recognition, behaviorally irrelevant) backgrounds. This weakness in the brain's 'active ignoring' of things or events that do not matter in noisy visual or tactile or other environments has been identified as a linchpin deficit for older humans. Indices of this weakness in 'active ignoring', for example, have been shown to be highly correlated with the magnitudes of memory and other cognitive losses in older humans.

Accordingly, methods and tools to for enhancing cognition are needed. The present disclosure provides methods and tools for improving the cognitive ability in suppression of irrelevant stimuli.

SUMMARY

The present disclosure relates to methods and tools for enhancing cognition in an individual. The methods involve presenting to the individual multiple sets of stimuli. Each set of the multiple set contains two or more stimuli and at least one set of the multiple sets contains a target stimulus. The method then receives an input from the individual, and informs the individual as to whether the input is a correct response. The methods encompass iterations of stimuli presentation, receiving of the input, and lastly, generation of feedback to the individual until the individual learns and retains what the target stimulus is.

DETAILED DESCRIPTION OF EXEMPLARY EMBODIMENTS

Figure 1:
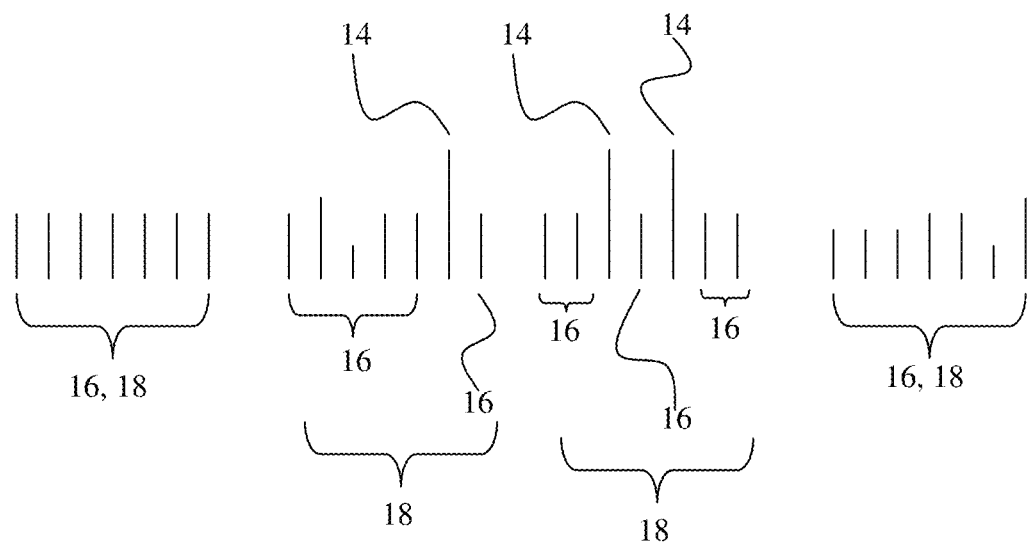
FIG. 1. A graphical representation of four sets of auditory stimuli employed in the methods of the present disclosure.

The present disclosure relates to methods for enhancing cognition in an individual. The methods involve presenting to the individual multiple sets of stimuli. Each set of the multiple set contains two or more stimuli and at least one set of the multiple sets contains a target stimulus. The method then receives an input from the individual, and generates a feedback to inform the individual as to whether the input is a correct response. Where the presentation of the target stimulus is new to the individual, the individual is not initially informed of anything related to what the target stimulus is prior to the presentation. Thus, the individual provides inputs on a trial-and-error basis in iterations of the aforementioned steps in an attempt to learn what the target stimulus is.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

DEFINITIONS

When describing the methods and compositions of the present disclosure, the following terms have the following meanings unless otherwise indicated.

When describing the methods and compositions of the present disclosure, the following terms have the following meanings unless otherwise indicated.

The term "cognition", as used herein, refers to the speed, accuracy and reliability of processing of information, and attention and/or memory.

As used herein, the term "attention" refers to the facilitation of a target and/or suppression of a non-target over a given spatial extent, object-specific area or time window.

The term "gap" or "inter-stimulus-interval (ISI)", refers to a specified amount of time between ceasing presentation of a stimulus and presenting a next stimulus in a sequence.

The term "emphasis level", refers to a degree of distinguishability of the presented stimulus with respect to a background of stimulus.

The term "target stimulus", as used herein, refers to a stimulus that is arbitrarily chosen by the subject method or device to be the target stimulus among a group of stimuli presented to an individual. The target stimulus differs in at least one property from irrelevant stimuli. The target stimulus is initially unknown to the individual who eventually learns to identify the target stimulus through trial and error based on the feedback given by the subject method or device.

As used herein, the term "irrelevant stimulus" refers to a stimulus that is not the target stimulus due to difference in at least one or more different properties. The irrelevant stimuli may sometimes be referred herein as background stimuli. An irrelevant stimulus differs from a target stimulus but is not necessarily the same as another irrelevant stimulus.

Stimulus

The present disclosure relates to methods and tools that enhance cognition. Enhancing cognition includes improving the ability to learn and to retain the attributes of a target stimulus and the ability to suppress irrelevant stimuli.

The method requires presenting to an individual multiple (e.g. two or more) stimulus sets. A stimulus set may be auditory, visual or olfactory. Below are descriptions of some examples of stimuli that can be used in the subject methods.

Auditory

An auditory stimulus refers to a sound and may be characterized by, for example: frequency, loudness (i.e. intensity), timbre, or any parametric combination of these or any other sound features. The duration of time an auditory stimulus is presented to an individual can be varied. For example, an auditory stimulus may be presented to an individual, e.g. for a fraction of a second (such as about 40 milliseconds (ms), about 50 ms, about 60 ms, about 70 ms or more), for a second or for a length between about 1 and about 2 seconds or for up to about 2 seconds or more. An example of a duration of an auditory stimulus presentation is about 100 ms.

A stimulus can also be spectrally-complex stimuli like vowels, phonemes, syllables, or words. A stimulus can also be presented by a voice and as such characterized by the presenting voice (e.g. call of a specific bird). The auditory stimulus can also be characterized by a waveform that is defined by amplitude (i.e. intensity or loudness), frequency, or any other sinusoidal properties.

A target auditory stimulus can differ from an irrelevant auditory stimulus in any one or more of the characteristics, such as frequency, loudness, or timbre, as well as properties of these characteristics. For example, if they differ in frequency, the difference in frequency may be measured in hertz or octave. Hertz (Hz) measures the numbers of cycle per second in the sound wave while octave represents frequency as pitch. One octave refers to the interval between a first pitch and a second pitch, in which the first and second pitch differs by double or half the frequency of the first pitch. An auditory stimulus presented in the subject method may be between about 20 Hz to about 100 Hz, about 100 Hz to about 500 Hz, between about 500 Hz to about 1000 Hz, between about 500 Hz to about 2000 Hz, between about 2000 Hz to about 5000 Hz, between about 2000 Hz to about 8000 Hz, between about 8000 Hz to about 10,000 Hz, between about 10,000 Hz up to about 20,000 Hz or more. For example, the stimuli provided in the subject method may have a frequency from about 400 Hz to 4000 Hz or 1000 Hz to 6000 Hz.

The frequency difference between an irrelevant auditory stimulus and a target auditory stimulus may be between about 0.01 to about 0.05%, between about 0.05% to about 0.1%, between about 0.1% to about 0.3%, between about 0.3% to about 0.5%, between about 0.5% to 1%, between about 1% to about 3%, between about 3% to about 6%, up to about 9% or more.

Where the difference between an irrelevant auditory stimulus and a target auditory stimulus differs in loudness, the difference can be expressed in sound pressure level (SPL) measured in decibels (dB) above a standard reference level. The standard reference level is about 20 µPa. Where the auditory stimulus is represented as a waveform, loudness can be equivalent or proportional to amplitude. The loudness difference between an irrelevant auditory stimulus and a target auditory stimulus may be about 0.1 dB, about 0.5 dB, about 1 dB, about 2 dB, about 3 dB, about 4 dB, up to about 5 dB or more.

An irrelevant auditory stimulus may also differ from the target auditory stimulus in timbre, which is the quality of a sound that distinguishes different types of sound production, such as voices or musical instruments. The physical characteristics of a sound that mediate the perception of timbre include spectral and time envelopes. Spectral envelope refers to the boundary and shape of waveform while the time envelope characterizes the rise, duration, and decay of the wave. Timbre of a sound can also be referred to as tone quality or tone color. For example, the anomalous stimulus can differ from the background stimuli because it is presented by a call of a different bird of the same species, of a bird of another species, of a bird in another location, or any parametric variations thereof.

Other ways in which the irrelevant auditory stimulus may also differ from the target auditory stimulus can involve the various phonemes (e.g. vowels and consonants) in languages and combinations thereof that results in spoken words and/or syllables. For example, background stimuli can be specific phoneme while the anomalous stimulus can be a perceptually different but confusable phoenem or a different acoustic variant of the same phoenem. Details of how phonemes can be characterized can be found in U.S. Pat. Nos. 6,290,504, 6,261,101, and 6,413,098, disclosures of which are incorporated herein by reference.

Any of the characteristics of sound described above, and combinations thereof, can be one or more of the ways in which the target auditory stimulus may differ from the irrelevant au auditory stimulus.

Visual

A visual stimulus is made up of electromagnetic waves in the visible light spectrum and may be characterized by, for example: brightness, color, shape, surface texture, orientations (e.g. grating), location in a visual field, orthographic (e.g. textual), quantity, or motions, as well as properties of these characteristics. For example, a visual stimulus may be the number "5" or a geometric shape of a triangle, or a red sphere. Another example of a visual target stimulus can be a face amidst a crowd of faces of different genders, of different ages, of different ethnicities, presented at different visual field locations, or any parametric variations thereof. A target stimulus can also be a visual image of a bird of a certain species amidst a background of birds of the same or other species and at different spatial locations. A target visual stimulus may differ from an irrelevant visual stimulus in one or more of those listed properties.

Each stimulus may also be referred herein as a graphical element. Images may also be rich so as to contain multiple shapes, colors, textures, etc., as seen in a photograph or digitally-generated picture. Additional examples of how a target stimulus can differ from the irrelevant stimuli are provided below.

The target stimulus can contain an object in a different location and/or context from the same object in background stimuli. The target graphical element may not belong in the same category as the background elements. Different parts of an object may also be presented to the individual as stimuli in series, in which the individual needs to identify a part that does not appear in a correct location as the target stimulus. A background image can constantly be presented in the individual, in which the individual needs to detect a change in the image as the target stimulus. The target stimulus can be made more and more similar (in physical/semantic attributes) to the irrelevant, as time passes to increase difficulty level. The followings are some examples of an anomalous stimulus and background stimuli. The anomalous stimulus to be detected could be a car (or person travelling at a different speed or in a different direction than a group of car (or people) moving in a similar fashion. Another example could be to detect a visually presented number or letter ("5" for example) in a sequence non-letter shapes similar in appearance.

Similar to an auditory stimulus, the visual stimulus can also vary by the duration of time it is presented to an individual. Each graphical element may be presented with a specific duration to an individual, e.g. for a fraction of a second, for a second or for a length between about 1 and about 2 seconds or for up to about 2 seconds or more.

Olfactory, somatosensory, etc.

An olfactory stimulus is a chemical that can be bound by odorant binding protein or chemoreceptors. The odorant can be volatile and can diffuse in air to the nasal passages, for example. The olfactory stimulus may differ based on the type, the concentration of a chemical compound, or the odorant stimulus delivery time. Background odorants can be constantly presented to the individuals, in which the individual needs to detect a change in either of the odorant properties (type/concentration, duration) as the target stimulus. The target stimulus can be made more and more similar to the irrelevant stimulus as time passes to increase difficulty level.

Some common odorants include esters, terpenes, and aromatics. For example, an olfactory stimulus may be benzaldehyde, which is an almond-like fragrance to humans. In another example, the anomalous odorant stimulus to be detected (target) could be the smell of a spice (e g vanilla produced by the aromatic compound vanillin) that would be presented simultaneously with several other odorants having a smell associated with fruits. The fruit odors could be produced using ester such as octyl acetate (orange), isoamyl acetate (banana, pear) and pentyl butyrate (pear, apricot).

Similar to the auditory, visual and olfactory stimuli, somatosensory/tactile stimuli. Somatosensory/tactile stimuli may be employed in the subject methods. Somatosensory stimuli can vary in several properties, such as vibration strength, duration, spatial location, frequency, and combinatinatorial patterns of these parameters. Somatosensory stimuli used can also include light touch, vibration, temperature, and joint position. Other somatosensory stimulus properties would include raised or depressed shapes or textures on a surface, vibration strength and frequency, or limb position in space. For example, one different and four identical raised dot patterns could be gently applied in random order to the five fingers of one hand. The individual would be instructed to identify the finger being presented the anomalous stimulus and/or to identify the qualities of the anomalous stimulus itself.

Stimulus Set

Referring to FIG. 1, a stimulus set 18 is a sequence of stimuli presented to an individual with the same or similar inter-stimulus-interval (ISI). The ISI of a set can often be a fraction of a second, such as about 600 milliseconds (ms), about 500 ms, about 400 ms, about 300 ms, about 200 ms, or about 100 ms or less. The stimulus set can be delivered at a speed measured in pulse per seconds (pps). The stimuli in a set can be presented in about 1, about 2, about 2.5, about 3, about 3.5, about 4, about 5, about 6, about 7, about 8, about 10, about 12, about 15, about 20, about 25, up to about 30 or more pps. Each set contains at least two stimuli. For example, each set can contain about 3, about 4, about 5, about 6, about 7, about 8, about 9, about 10, about 15, about 20, or up to about 30 or more stimuli. Where the set contains 3 stimuli, the set may be referred herein as a triad. Where the set contains a target stimulus 14, the set contains at least one target stimulus in the sequence and can contain about 2, about 3, up to about 4 or more repetitions of target stimuli in the sequence. The number of target stimuli 14 is usually less than the number of total stimuli in a set. Where there are more than one target stimulus, each target stimulus may or may not be the same as each other in one or more properties of a characteristic.

The one or more target stimuli can appear at any location within a stimulus set.

Alternatively, the subject methods can also be carried out where the stimuli are presented to an individual in a continuous stream, such that a training block contains one long set of stimuli with a specific ISI. In this way, there is no inter-set interval and no onset-to-onset time within a training block. The one or more target stimuli can be presented with random occurrence in this stream. Where the stimuli within a training block are presented in a continuous stream, the irrelevant stimuli can be tonal or be acoustically complex (e.g. containing one or more different properties in one or more characteristics described above). The irrelevant stimuli can also be a noise (e.g. white noise). The properties in one or more characteristics of the irrelevant stimuli and/or target stimuli can also vary after a discrete amount of time (e.g. after the individual has achieved 90% correct response rate).

All the irrelevant stimuli in a set may be identical or different in one or more properties among the irrelevant stimuli. See a graphical representation of irrelevant auditory stimuli 16 in FIG. 1. As seen in FIG. 1, some irrelevant stimuli are similar if not identical but some differ from each other. All the irrelevant stimuli, however, differ in at least one or more properties from target stimuli 14. Where the auditory stimulus set contains one or more target stimuli, target stimuli 14 can appear more than once in a set and can be presented at any random location in the sequence of the set. Again, with reference to FIG. 1, the second and third sets in the order from left to right contain 1 and 2 target stimuli 14, respectively. As noted above, the target stimulus can differ from the irrelevant stimuli in a number of different ways. For example, the target stimulus can be 12 kHz while the irrelevant stimuli can be 11 kHz, 10 kHz, or 9 kHz.

Where the stimuli are visual, a visual stimulus set presents a sequence of graphical elements to an individual in which the set can contain exclusively of irrelevant stimuli or contain one or more target stimuli. A visual stimulus set is a sequence of graphical elements with the same or similar inter-stimulus-interval (ISI) in the same fashion as described above for an auditory stimulus set. For example, each graphical element may be presented for duration of about 1 second with an ISI of about 1 second. As an example, an irrelevant visual stimulus set may contain varied geometric shapes, each of the same or different colors, all rotating clockwise. In a corresponding example, where the visual stimulus set contains a target stimulus, the set may contain a geometric shape rotating counterclockwise, so the motion attribute of the target stimulus differs from the motion attribute of all the irrelevant visual stimuli.

A stimulus set can also contain a combination of stimuli of different sensory systems. For example, a stimulus set may combine both auditory and visual stimuli. The set may present a sequence of auditory and visual stimuli that can be synchronized or unsynchronized. A target set can contain either a target auditory or a target visual stimulus or both. For example, an irrelevant stimulus may be the number "5" with horizontal gratings as the texture as well as an auditory stimulus of a vowel. A corresponding target stimulus set can contain the number "5" with vertical gratings as the texture as well as an auditory stimulus that is the same or different from that of the irrelevant stimulus.

Methods

As noted above, the methods of the present disclosure enhance cognition by training an individual to suppress irrelevant stimuli. The method involves presenting to an individual multiple sets of stimuli (referred to herein as "multiple stimulus sets"). The stimulus sets include auditory stimuli, visual stimuli, olfactory, or a combination thereof, as described above. In one embodiment, with reference to FIG. 2, the subject methods involve presenting 2 to an individual multiple sets of stimuli (e.g. two or more sets). Each set of the multiple sets contains two or more stimuli. In the multiple sets presented to the individual, at least one set contains at least one target stimulus, where such set is sometimes referred to as the "target set". Where the method is carried out for the first time for an individual (e.g. The first cycle in a training session), prior to presentation of the stimuli, the individual is not informed of the target stimulus or its properties. As such, the individual is not informed as the distinction between an irrelevant stimulus and the target stimulus. In initial cycles, the individual is likely to have to guess the identity of a target stimulus and provide an input accordingly. The method then generates an output to inform the individual whether or not the input is correct. By presentation of the multiple stimulus sets and trial and error, the individual can be trained to learn and retain the target stimulus.

Alternatively, it would also be appreciated that the method can encompass a step prior to the presenting step 2. In this additional step, the individual can be informed of the identity of the target stimulus (e.g. being presented the target stimulus) prior to being presented the multiple sets of stimuli.

Figure 2:
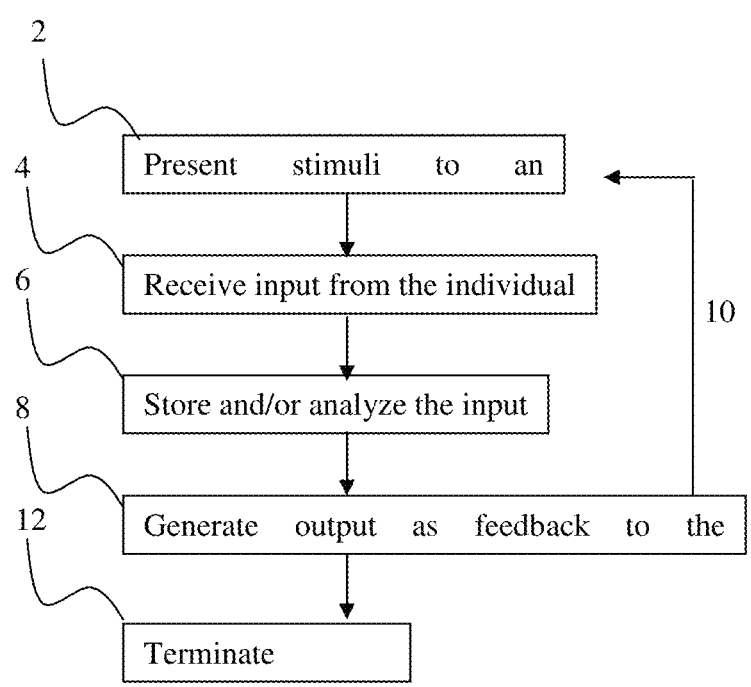
FIG. 2. Flow chart of an example of a method for cognitive training in accordance with the present disclosure.

As noted above, where at least one set of the multiple sets contains at least one target stimulus. The target stimulus is randomly selected for each training session. The target stimulus may also change within a training session and the details will be discussed later below. Wherein there is more than one type of target stimuli in the multiple sets, the two or more target stimuli may differ from each other in one or more properties. With reference to FIG. 2, the method also receives 4 an input from the individual that has been instructed to respond to or guess the target stimulus. As discussed above, an irrelevant stimulus can be identical to or different from other irrelevant stimulus in at least one or more properties. However, all irrelevant stimuli differ from all target stimuli in at least one or more property (e.g. pitch).

After receipt of the input, the subject methods store and/or analyze the input to determine if the input correctly identifies the target stimulus. The method then generates an output to inform the individual if the input is correct. The output may be auditory feedback, such as sound (e.g., a "thunk" or silence for an incorrect input and a "ding" for a correct input) or visual feedback (e.g., a graphical indication of having received a correct input or not). Either an auditory or a visual output may also inform the individual a score that has increased, decreased, or remained the same in the number of points, as an indication of whether the input is correct or not.

As seen in FIG. 2 and noted above, the method involves presenting multiple sets of stimuli to an individual. The inter-set interval and the onset-to-onset time are longer than the inter-stimulus-interval (ISI) described above. The inter-set interval can be less than 1, about 2, about 3, about 4, about 5, about 9, up to about 10 or more seconds in length. The time interval between the first stimulus of one stimulus set and the first stimulus of the next stimulus set that immediately follows is referred to as "onset-to-onset time". Onset-to-onset time is often a fraction of a second and is more than ISI. Examples of onset-to-onset time can be about 1 sec, 600 milliseconds (ms), about 500 ms, about 400 ms, about 300 ms, about 200 ms, or less.

The subject methods also involves repeating 10 the aforementioned steps of presenting 2 the multiple sets of stimuli, receiving 4 an input from the individual, storing/analyzing the input 6, and generating an output 8 to inform the individual whether the input is correct. When steps 2, 4, 6, and 8 are carried out in a sequence, these steps combine to form a cycle. Repeating step 10 once is then referred to as carrying out the cycle once. The cycles can be iterated with the same stimuli or different stimuli. For example, where the stimuli are auditory, the irrelevant stimuli and the target stimuli may be the same or different in one or more properties (e.g. loudness) as the corresponding stimuli in the previous cycle. In another example, any cycle of the subject method can be exclusively auditory, exclusively visual, or a combination of both in any location in an iteration sequence. Thus, one cycle may differ from the previous cycle because one is auditory and the other is visual. There may also be two or more consecutive cycles in which the stimuli are exclusively auditory, exclusively visual, or a combination of both.

A training block is made up of two or more cycles. The time lapse between each cycle in a training block can vary and can be longer than or the same as the inter-set interval. The time interval between each two cycles and the number of cycles can be selected to tailor different training blocks.

A training block is made up of iterations of cycles in order to achieve a pre-determined goal. A predetermined goal may be dependent on the responses of the individual or the length of the training block. For example, the training block iterates the cycles as long as the individual has not learned what the target stimulus is and halts once the individual has identified the target stimulus with a level of proficiency, e.g. only true hits and no false positives, a certain percentage of true hits, or inputting true hits consecutively for a number of times).

Alternatively, the training block can repeat as many cycles as necessary to train the individual to perform at a certain level, measured by one or more indices. Since the methods involve trial and error, especially in the beginning stages of presenting a target stimulus previously unknown to the individual, the amount of time or number of stimulus sets that is require for an individual to learn and to retain the target stimulus is an index that can be measured and stored to evaluate the performance level of the individual. Another index that can be used to measure performance is the amount time the individual takes to respond after the presentation of a target stimulus. Other indices can include, for example, reaction time, response variance, correct hits, omission errors, false alarms, signal detection d-prime, learning rate, and/or performance threshold, etc.

As an example, a training block may repeat as many cycles as it is necessary for the individual to attain at a level of proficiency in which any target stimulus previously unknown to the individual can be identified within 10 occurrences of the target stimulus, or within 30 seconds, for example. The training block can also repeat the cycles until the ratio of true positives to false positives in the latest number of cycles is at or above a selected threshold. For example, the training block may terminate 12 when true positives/negatives significantly outweigh the false positives/negatives in the last 5 minute or the last 10 cycles. Alternatively, the training block may terminate 12 regardless of the correctness of the inputs after a select duration of time (e.g. about 5 minutes, about 10 minutes, about 15 minutes, about 20 minutes, about 30 minutes, up to about an hour or more). A combination of the thresholds or factors can also be used to decide when the iterations should be stopped.

The method also includes repeating one or more training blocks. The time lapse between training blocks can range from a few seconds, an hour, a day, or more. Accordingly, the individual may receive a training block a specified number of times each day, for a specified number of days. In other words, the individual may go through a plurality of training blocks with a selected frequency (e.g. one training block daily) over a period of days or months (e.g. 6 months) to improve cognition.

The target stimulus can change during a cycle or a training block. The individual can be made aware of the change solely by the output/feedback step 8 (as seen in FIG. 2) that informs whether the stimulus chosen by the individual is the target stimulus. The target stimulus changes to provide a variety of trials and thus different challenges to the individual. The variety also trains the individual to learn and suppress different types of stimuli. The change in target stimuli and/or irrelevant stimuli can also allow the evaluation of an individual's sensitivity toward different types and/or categories of stimulus. For example, an individual may be less sensitive to a range of auditory frequencies and that the decreased in sensitivity may be unrelated to cognitive ability.

When the target stimulus changes, the difficulty level may also changes. The difficulty level of each cycle and/or training block can differ among cycles and/or training block throughout the repetition of cycles and/or repeating training blocks. As such, difficulty levels can change inter- or intra-training block. If an individual achieves a threshold level of success (e.g. a pre-determined percentage of correct responses), the difficulty of the cycle and/or training block may be increased relative to the previous cycle and/or training block. Conversely, if the individual achieves a specified level of failure or fails to achieve a level of success, the difficulty of the cycle and/or training block may remain the same or decrease relative to the previous cycle and/or training block. Where the subject methods involve presenting stimuli in a continuous stream in a training block, the difficulty level can change at random locations within the training block.

In an initial cycle and/or training block, the individual can be presented with a default difficulty level and the difficulty level can increase, decrease, or remain the same until the training block terminates after a predetermined goal is attained. A difficulty level can be increased in a number of following ways. One way is to decrease the window of response, which is the time period between the moment a stimulus set is presented and the onset of the subsequent stimulus set. The window of response can be the onset-to-onset time. Alternatively, the window of response can also be the time period between the moment a stimulus set is presented and an amount of time afterwards determined by the methods. The individual has this window of time to respond as instructed. Hence, decreasing the ISI, the inter-set interval, the duration of the stimulus, window of response, or any combinations thereof are ways to increase difficulty. Another way to increase difficulty is to minimize the difference between irrelevant stimuli and the target stimuli. For example, a target auditory stimulus that differs from irrelevant auditory stimuli by about 1% in frequency is more difficult than if the frequency difference is 3%. In a related example where frequency is varied to increase difficulty levels, the difference in frequency between target and irrelevant stimuli is reduced in base 2 logarithmic steps starting at 0.5 octaves for level one difficulty to 0.02 octaves at level 6 difficulty. Another way to increase difficulty level is to combine stimuli from different senses (e.g. visual and auditory). Having more than 1, more than 2, more than 3 or more different types of target stimuli in one training block can also increase difficulty as the individual need to learn and retain properties pertaining to more than 1 target stimulus.

One other way to vary difficulty level is to change the duration of the stimulus, of the cycle, and/or of the training block. Where the subject methods present stimuli in a continuous stream, a training task variable to modulate difficulty level can be the length of the continuous stream of stimuli. For example, the length of the continuous stream in a training block may be about 5 minutes, about 10 minutes, about 15 minutes, about 20 minutes, up to about 30 minutes or more.

An additional way to vary difficulty is to increase or decrease the loudness of the stimuli. Alternatively, a variable that can be employed is the frequency of appearance of the target stimuli.

Where the stimuli are visual, the following are descriptions of how some variables can change within a cycle or a training block to change difficulty levels. One example is to morph images so that the target graphical element becomes more and more similar to the irrelevant stimuli. Where the individual needs to detect an target stimulus appearing in a background image, the target stimulus can be made more and more similar (in physical/semantic attributes) to the irrelevant stimuli as time passes. Any one or combinations of these ways to increase difficulty can be used in the subject methods.

The difficulty level can be adjusted as frequently as needed and can also be tailored for a predetermined goal or to the ability of the individual. The individual can start at the lowest difficulty level for the first training block on each day, at the difficulty level determined by previous training blocks, or at the difficulty level of their choosing. The individual may be presented with the same difficulty level cycles and/or training blocks until a certain level of success or failure is reached. The difficulty level can also decrease, increase, or remain the same, regardless of the performance of the individual. The methods can also be specifically tailored to the individual by maintaining around a threshold success rate for the individual, e.g., using a single stair maximum continuous performance likelihood procedure. For example, the methods can be tailored to target a constant error rate from an individual (e.g. approximately 80% correct trial response accuracy). Accordingly, with reference to FIG. 2, difficulty level can change any point after step 8 during cycle iterations depending on the predetermined goal.

The method may further include performing a trial block, where the trial block includes cycles of varying difficulty levels, and varying stimulus types, not necessarily in any order for the purposes of diagnosing cognitive and/or sensory abilities of the individual prior, during, and/or post-training.

The methods can further include a demonstration of the type of stimulus to be presented and how to input a response prior to running a cycle and/or training block. Instructions can provide an exercise to familiarize the individual with the procedures of receiving the presentation of stimuli and with the procedures of inputting a response. The instruction can include details on the types of responses expected from the individual when presented with the target stimulus or in the absence of the target stimulus. The response can be a physical action of clicking a button and/or moving a cursor to a correct location on a screen, head movement, finger or hand movement, vocal response, eye movement, etc. Input or response from an individual received by the methods of the present disclosure involves a voluntary initiation of an action on the part of the individual and excludes measurements that may be obtained from an individual passively. For example, brain waves, such as those obtained in magnetoencephalography, are not considered as an input from an individual in the present disclosure. Optionally, prior to running a cycle and/or training block, the methods can sometimes present to an individual a description of the target stimulus or presenting the actual target stimulus.

With reference to FIG. 2, the present method includes determining and/or categorizing 6 responses, and generating output 8 to the individual, e.g. visually or audibly. The types of responses that can be received from the individual and examples of out are described in more detail below.

Hit (true positive): If the individual correctly indicates the presence or absence of one or more target stimuli in a stimulus set, the response is considered to be a hit. The response would also have to be received within the window of response. For example, the response could be an input via a user interface into a computer, remotely or locally. When the individual's response is a hit or true positive the individual may receive a feedback or output. The output may be a reward and can take various forms: auditory feedback, such as a success sound (e.g., a "ding"), visual feedback (e.g., a graphical success indication), addition of points, and/or bonus meter advances.

Non-response (true negative): If the individual correctly refrains from indicating the presence of a target stimulus in a stimulus set, i.e. due to the absence of a target stimulus, the individual's response is a non-response or true negative. The individual may be rewarded an output as described above for true positives. Output can include bonus meter advances, and after five non-responses in a row, for example, may be rewarded with auditory feedback, e.g., a success sound (e.g., a "ding"), visual feedback (e.g., a graphical success indication, progression of levels, such as a displayed "checkmark"), and/or addition of points.

False positive (false alarm): if the individual incorrectly identifies that an irrelevant stimulus in a stimulus set as the target, the individual's response is a false positive. In this case, the individual may receive a penalty as an output. The penalty can also take on the forms as described above: auditory feedback, such as an error sound (e.g., a "thunk"), visual feedback (e.g., a graphical indication of error or failure), bonus meter reset (where progress toward a bonus is reset to zero or decreased), lack of point addition or subtraction of points.

Miss (false negative): If the individual incorrectly failed to indicate the presence or absence of one or more target stimuli in a stimulus, the individual's response is a false negative. The subject may be penalized as described above for false positive responses with a bonus meter reset (where progress toward a bonus is reset to zero or decreased). Where the stimulus is visual, frame color may change, i.e., the graphical user interface (GUI) may modify the color of the region around the target stimulus or stimulus set to indicate an error. Other rewards or penalties may be used as desired, e.g., visual feedback, e.g., an "X" under the stimulus, resetting the bonus meter, and so forth.

If the response is unclear such that it cannot be categorized by the computer or other tools carrying out the subject method, the response can be categorized into false positive, false negative, or simply as an uncategorized/undetermined response.

Aside from determining the correctness or incorrectness of the individual's response, the method can also analyze, store, and output the reaction time for the response and/or any statistical measures for the individual's performance (e.g. percentage of correct or incorrect response in the last number of cycles, over a specified duration of time, or specific for a type of irrelevant and/or target stimuli, etc.).

The one or more different outputs of described above may or may not be presented to the individual after each cycle. Alternatively, output may be generated at the end of each training block or at the end of several training block. When and what output is generated can also be pre-determined by the individual and/or the operator of the training program.

The methods of the present disclosure may also be combined with other methods that aim to enhance cognition. For example, the training blocks of the subject method can alternate with training block of a second method for a combination training regimen.

The method may be designed to be presented to an individual in a form of game or challenge, in which instructions to an individual include game objectives and individual's input are scored. For example, a correct response increases points whereas the score remains unchanged or decreased in points if the response is incorrect.

The methods of the present disclosure encompass the addition of engaging game elements that are integrated with the training block. These game elements confer substantial benefits to the user or the training program. One benefit is that the game context may encourage the user to engage more attentional resources to task, which can be critical for enhancing cognition. Additionally, the game context can provide incentives for a user to pay attention and/or complete the training. In other words, the interest and goal orientation created by the game context provide incentive to continue training for longer periods of time than would generally be supported by the less engaging training task on its own. Game specific features that can increase incentive and interest of an individual may include but not limited to bonus points, in-game reward or penalty, such as a graphical or auditory representation thereof, rewards or penalties that scale with difficulty level or time spent, real life rewards, etc.

Target Population

Individuals that can use the methods and tools of the present disclosure can be any person, especially those interested in enhancing cognitive abilities.

Individuals that can benefit from the subject methods and tools include but not limited to adults, such as aging adults. For example, the subject methods and tools can be useful for adults that are about 40 years told, about 50 years old, about 60 years old, about 70 years old, up to about 80 years old or older. Measurable deterioration of cognitive abilities in an individual is common as he or she ages. The experience of this decline may exhibit as an occasional oversight in various tasks and/or increasing difficulty in concentration. The decline often progresses to more frequent lapses as one ages in which there is passing difficulty performing tasks requiring extraction of visual or auditory information from a noisy environment quickly and accurately. Avoiding dangers when driving a car, scanning a crowd for a familiar face, and reading quickly are a few of such examples.

Such decline typically accelerates at age 50 and older and over subsequent decades, such that these lapses become noticeably more frequent. It is often clinically referred to as "age-related cognitive decline". While often viewed (especially against more serious illnesses, e.g. Alzheimer's) as benign, such predictable age-related cognitive decline can severely alter quality of life by making daily tasks arduous.

Age-related cognitive decline can lead to a more severe condition now known as Mild Cognitive Impairment (MCI), in which sufferers show specific sharp declines in cognitive function relative to their historical lifetime abilities while not meeting the formal clinical criteria for dementia. MCI is now recognized to be a likely prodromal condition to Alzheimer's Disease (AD) which represents the final collapse of cognitive abilities in an older adult. The subject methods and tools have the potential to reverse and/or prevent the onset of this devastating neurological disorder in humans, such as those suffering or at risk for MCI.

Aside from age-related cognitive decline, people of all ages who experience or are at risk for cognitive impairment can benefit the subject methods and tools. For example, the subject methods are useful for training individuals whose cognitive losses have arisen as a consequence of injury, medical treatments, or chronic neurological or psychiatric illness. Specific examples that can cause cognitive impairment include traumatic brain injury, stroke, brain infections (AIDS, Lyme Disease, West Nile Virus, malaria, et alia), 'chemobrain', losses due to periods of anoxia due to surgery or injury, diffuse brain damage attributable to alcohol or drugs, etc. Cognitive losses of developmentally impaired child and adult populations can also be potentially reversed by the subject method.

For individuals suffering from chronic neurological and psychiatric illness, changes in inhibitory neuron populations, myelination, response slowing, emergent response dis-coordination, degradation of response selectivity in spatial, spectral and temporal detail, and the degradation of the distinctions between background and target stimuli are very similar to the effects of age-related cognitive decline. Accordingly, individuals of any age with profiles of cognitive impairment that parallel those in aging are target populations for the methods and tools of the present disclosure. The individuals can experience substantial 'corrective' neurological changes if trained by the subject methods.

Computer System and Tools

The present disclosure provides computer program products that can carry out the subject method of enhancing cognition. The subject matter described herein may be embodied in systems, apparatus, methods, and/or articles depending on the desired configuration. In particular, various implementations of the subject methods described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g. keyboard and/or mouse), and at least one output device (e.g. speaker, headphones, and/or display).

These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal.

Similarly, systems of the present disclose may also include a processor, such as CPUs, and a memory coupled to the processor. The system further includes a user interface (e.g. GUI) and one or more communication buses for interconnecting these components. The user interface includes at least one or more actuators (e.g. display or speakers) and one or more sensors, and may also include one or more feedback devices. For example, speakers or headphones may provide auditory prompting and feedback to the individual during execution of the computer program. Input devices such as a mouse or keyboard allow the individual to navigate the computer program, and to select particular responses after visual or auditory prompting by the computer program.

The memory may include one or more programs that cause the processor to perform one or more of the operations of the methods described herein. Memory may include high speed random access memory and may also include non-volatile memory, such as one or more magnetic disk storage devices. Memory may include mass storage that is remotely located from the central processing unit(s). The memory stores an operating system (e.g., Microsoft Windows, Linux or UNIX), an application module, and may optionally store a network communication module. Although a number of different computer platforms are applicable to the present disclosure, embodiments of the present invention execute on either IBM compatible computers or Macintosh computers, or similarly configured computing devices such as set top boxes, PDA's, gaming consoles, etc.

As noted above, the system may optionally include one or more networks or other communications interfaces, such as a network interface for conveying testing or training results to another system or device. The computer network contains computers, similar to the one described above, connected to a server. The connection between the computers and the server can be made via a local area network (LAN), a wide area network (WAN), or via modem connections, directly or through the Internet. A printer may also be connected to the computer in a network to illustrate that an individual can print out reports associated with the computer program of the present disclosure. The computer network 200 allows information such as test scores, game statistics, and other data pertaining to an individual's performance to flow from one computer to another, e.g. a server. Data pertaining to an individual's performance can include, fore example, reaction time, response variance, correct hits, omission errors, false alarms, signal detection d-prime, learning rate, and/or performance threshold, etc. An administrator can review the information and can then download configuration and data pertaining to a particular individual, back to the individual's computer. Alternatively, or additionally, the server may execute the computer program, and the individual may interact with the program via the individual's computer, e.g., in a client/server relationship.

As noted above, the individual may perform the training exercise via a graphical user interface (GUI), whereby graphical elements and/or sounds are presented to the individual and whereby the individual may provide responses. For example, the GUI may include the visual field within which various images, e.g., target stimulus set, may be displayed in a sequence to the individual, as well as various on-screen buttons or controls whereby the individual may interact with the training exercise. For example, the display may provide a start button in which the individual may press (e.g., click on) to begin or resume a training block. Additional GUI elements may also be provided, e.g., for indicating various aspects of the individual's progress or status with respect to the exercise or task, such as the difficulty level of the current training block. Examples include a bonus meter (or equivalent), which may indicate the number of correct responses in a row, a graphical element that flashes, a program that plays music, and/or award bonus points, when some specified number, e.g., 5, of correct responses is attained.

The application module executing the subject method may include one or more of the following: a) a stimuli generation control program, module or instructions, for generating multiple sets of stimuli, as described above for the subject method; b) an actuator or display control program, module, or instructions, for producing or presenting the multiple sets of stimuli to an individual; c) a sensor control program, module or instructions for receiving input by extracting raw data in the sensor signals indicative of the individual's response; the sensor control program, module or instructions may also include instructions for controlling operation of the one or more sensors; d) a measurement analysis program, module or instructions, for analyzing the individual's responses to produce measurements and analyses, as discussed above; and e) a feedback program, module or instructions, for generating feedback signals as output for presentation to the individual via the one or more actuators or feedback devices.

The application module may furthermore store data, which includes the measurement data for an individual, and optionally may also include analysis results and the like. The application module may also store data derived from theoretical users or actual users other than the individual. Such data may be used as normative data from one or more control groups of individuals, and optionally may also include analysis results, and the like, based on the measurement data from the one or more control groups. Any of the programs described above may be stored or executed from more than one locations, e.g. more than one computer readable medium. For example, the stimuli generation program may be executed remotely via a network while the measurement analysis program may be stored and/or executed locally.

As noted above, the subject method can be employed as computer-based exercises and tasks in order to renormalize and improve an individual's cognition, e.g., the efficiency and capacity of suppressing irrelevant stimuli. Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results.

In one embodiment, for example, there is provided a computer-readable storage medium, comprising instructions executable by at least one processing device that, when executed, cause the processing device to: (a) present to an individual multiple sets of stimuli, wherein each comprises two or more stimuli, wherein at least one set of said multiple sets comprises a target stimulus; (b) receive an input from said individual; (c) determine whether said input is a correct response to the presented stimuli; and (d) inform said individual as to whether said input comprises a correct response. The computer-readable storage medium may further comprise instructions executable by at least one processing device that, when executed, cause the processing device to repeat said presenting, said receiving, and said informing, wherein target stimulus is presented at least two times to said individual. The repeating may be terminated where the percentage of correct or incorrect inputs is the same or greater than a selected threshold. Alternatively, the repeating may be terminated after about 60 minutes. Each of said multiple sets may be a group of three stimuli. The computer-readable storage medium may further comprise instructions executable by at least one processing device that, when executed, cause the processing device to determine a difficulty in discerning a target stimulus, and increasing or decreasing the difficulty based on said input. In one embodiment, there are two or more target stimuli.

In an alternative embodiment, the computer-readable storage medium may further comprise instructions executable by at least one processing device that, when executed, cause the processing device to generate an output. The output may be a reward or a penalty. The stimuli may be auditory and/or visual. The target stimulus differ in frequency, loudness, timbre, color, shape, size, texture, orientation, motion, and/or any combination thereof.

The following examples further illustrate the present invention and should not be construed as in any way limiting its scope.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Materials and Methods

The following methods and materials were used in the Examples below.

All procedures were approved under University of California San Francisco Animal Care Facility protocols. Nineteen male young (6-12 months old) and seventeen male aged (26-32 months old) Brown-Norway rats obtained from the National Institute on Aging (NIA) colony were used for this study. These rats were housed in pairs and wooden objects, plastic tunnels and toys were added to the cage for enrichment. Nuts and other food elements appreciated by this specie supplemented their diet on an intermittent basis. Experimental animals and untrained controls were slightly food deprived to increase exploratory behavior and motivation to perform the food-rewarded training task. Their weight was not allowed to decrease by more than ten percent of their initial weight. Their auditory environment consisted mainly of sounds and vocalizations produced by nearby rats of the colony. Background noise levels were negligible in the housing area. Aged rats were kept for at least one month in this environment before any manipulation.

For mapping, the rats were pre-medicated with atropine sulfate (0.02 mg/kg) to minimize bronchial secretions and with dexamethasone (0.2 mg/kg) to minimize brain edema. They were then anesthetized with pentobarbital (35-60 mg/kg, i.p.). Supplemental doses of dilute pentobarbital were given as required to maintain the rat in an areflexic state while preserving a physiological breathing rate. The cisterna magnum was drained of cerebrospinal fluid to minimize cerebral edema. The skull was secured in a head holder leaving the ears unobstructed. The right temporalis muscle was reflected, auditory cortex was exposed and the dura was resected. The cortex was maintained under a thin layer of silicone oil to prevent desiccation. Recording sites were marked on a digital image of the cortical surface.

Cortical responses were recorded with tungsten microelectrodes (1-2 MOhm; FHC, Bowdoinham, Me.). Recording sites were chosen to sample evenly from the auditory cortex at inter-electrode distances of 125-175 µm. At every recording site, the microelectrode was lowered orthogonally into the cortex to a depth of 470-600 µm (layers 4/5), where vigorous stimulus-driven responses were obtained. The neural signal was amplified (10,000×), filtered (0.3-3 kHz), and monitored on-line. Acoustic stimuli were generated using TDT System III (Tucker-Davis Technology, Alachua, Fla.) and delivered to the left ear through a calibrated earphone (STAX54) with a sound tube positioned inside the external auditory meatus. A software package (SigGen and Brainware; Tucker-Davis Technology, Alachua, Fla.) was used to generate acoustic stimuli, monitor cortical response properties on-line, and store data for off-line analysis. The evoked spikes of a single neuron or a small cluster of neurons were collected at each site.

Behavior

The operant learning paradigm described below was designed based on standard published procedures (Polley, D. B., Steinberg, E. E. & Merzenich, M. M. (2006) *J Neurosci* 26: 4970-4982). Lightly food deprived young adult or aging rats were rewarded with a food pellet for making a "Go" response shortly after the presentation of a target stimulus. Training was performed in an acoustically transparent operant training chamber (20×20×18 cm, length×width×height) contained within a sound-attenuated chamber.

Example 1 Effects of Training in Rats and Humans

Neural recordings from auditory cortex were obtained from trained and untrained aging rats. The results shown in panel A of FIG. 3 were normalized firing rates for either target stimuli (target; left) or irrelevant stimuli (distractors; right). For aged rats, neural firings in response to irrelevant stimulus distractors were significantly suppressed post-training.

Figure 3:
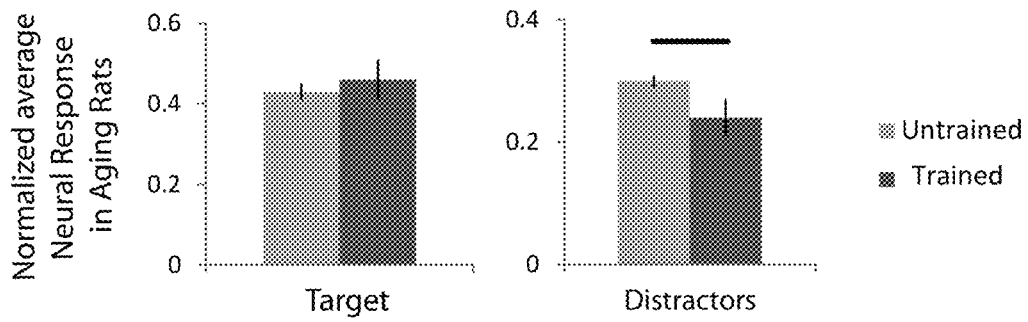
FIG. 3. Panel A, Neural recordings from auditory cortex of aging rats. Panel B, Performance improvement in irrelevant stimulus suppression training Panel C, Performance variance in irrelevant stimulus suppression training Panel D, Training effects on the auditory evoked potential (EEG) to irrelevant distractors in an aging human. Dark plot is the EEG observed during target identification phase while the light gray plot is the EEG observed during the background distractor suppression phase.
Figure 3:
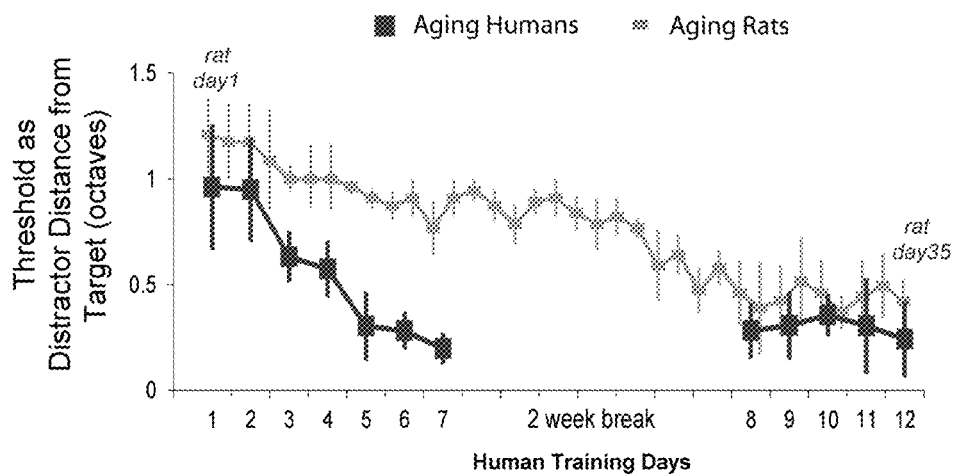
Figure 3:
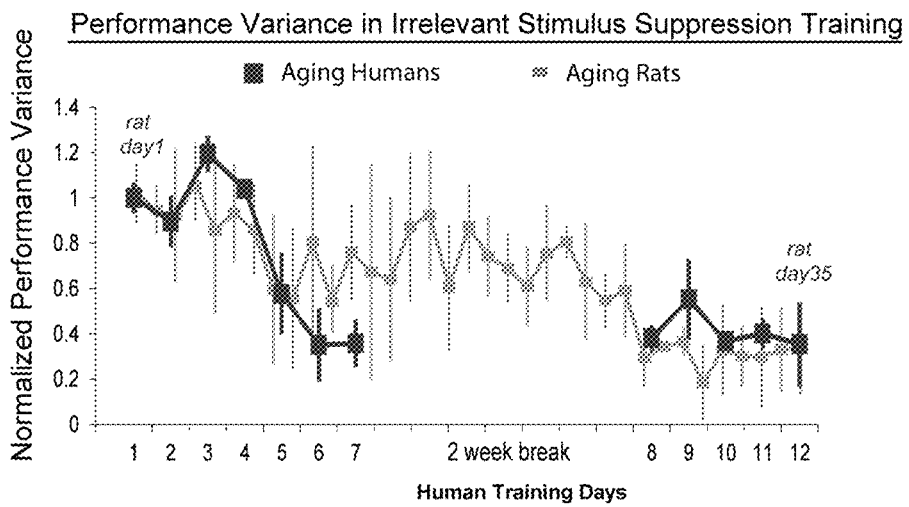
Figure 3:
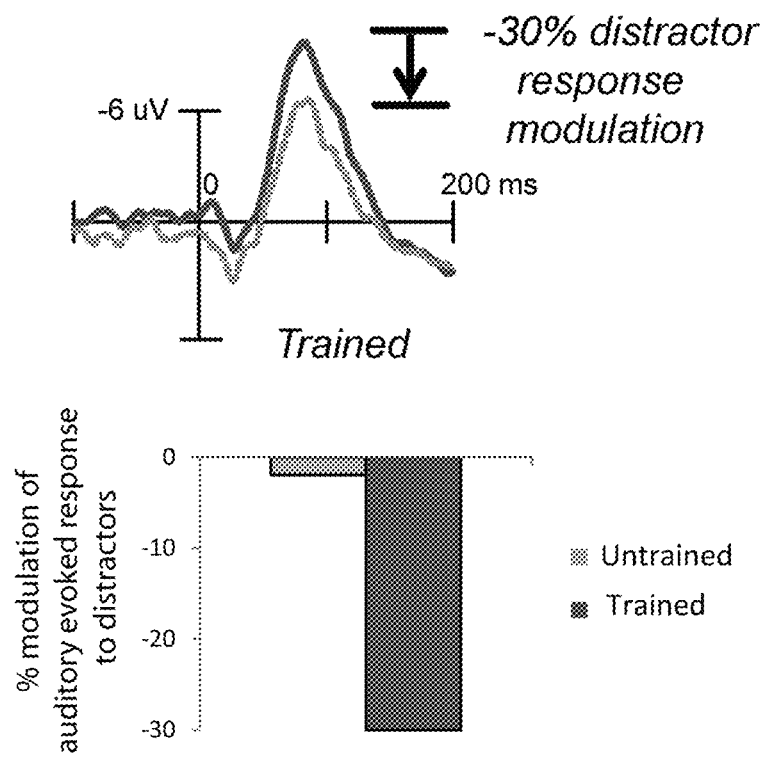

Performances in aging humans (n=2) and aging rats were monitored using a threshold at which target stimuli were correctly identified. The thresholds were distances between an auditory target stimulus and irrelevant stimuli in octave units. The performances were monitored over 7 days (21 sessions, 3 per day) of training, and maintenance of trained performance levels after a two week break period (36 total sessions). The results shown in panel B of FIG. 3 show steady performance improvement throughout the duration of this experiment. Similarly, aging rats (n=3) also learned the method over 35 consecutive days/sessions of training.

Reliability of performance was also evaluated in aging humans and aging rats (panel C of FIG. 3). Reliability of performance were measured as function of reducing performance variability and was found to significantly improve with training in aging humans and rats as depicted.

Training was also found to have effects on the auditory evoked potential (EEG) in response to irrelevant stimuli in aging humans. In the potential seen in panel D of FIG. 3, the dark plot is a potential observed during the target identification phase of training and the light gray plot is the potential observed during the background distractor suppression phase—after the target-irrelevant stimulus difference has been identified by the individual. The auditory evoked potential showed improved post-training neutral capacity to differentially modulate distractor response (n=1) (panel D of FIG. 3). About 30% modulation can be seen in the response to the irrelevant stimulus (right side of panel D).

These data provide supporting evidence in both rats and humans for the first model versions of the training methods, in which elemental auditory tonal stimuli were employed. These versions of the method in their elemental form allowed for direct comparison of research findings between the aging human and rat populations. In rats, the training method is able to refine auditory processing towards background distractor suppression (n=1 rat: 14 neurons) (A). Aging humans as well as rats successfully and reliably learn the training method (panels B and C of FIG. 3). In the human tested, a large negative modulation of neural responses to background distractors was observed only post-training (panel D of FIG. 3).

Example 2 Cognitive Assessment Measures

Ways in which behavioral and neurological impacts of auditory (tonal) versions of the subject methods in humans may be assessed are described below.

To broadly assess alterations in neuropsychological function and the generalizability of the effects of training on these measures, a set of standardized cognitive tests are performed before and after training blocks (for the training group as well as for a no-contact control group). Published normative data for these standardized assessments can provide a basis for defining performance deficits. Examples of assessment for various cognitive abilities are listed below, protocols of which are known in the art.
a) Attention: Sustained Attention to Response Task (Robertson et al. (1997) *Neuropsychologia* 35:747-58), Test of Variables of Attention (TOVA) (Greenberg et al. (1993) *J Child Psychol Psychiatry* 34:1019-30), Digit Vigilance (Kelland et al. (1996) *Arch Clin Neuropsychol.* 11:339-44);
b) Working Memory: Letter Number Sequencing (WAIS III; Wechsler D (1997) *Wechsler Adult Intelligence Scale—Third Edition*. San Antonio, Tex.: The Psychological Corporation), Auditory Consonant Trigrams (Stuss et al. (1987) *Clinical Neuropsychologist* 1:139-152), Filter Task (Ophir et al. (2009) *Proc Natl Acad Sci USA.* 106:15583-7); Word-in-Noise task (Wilson (2003) *J Am Acad Audiol.* 14:453-70)
c) Executive Function: Delis-Kaplan (D-KEFS) Stroop Test (Delis et al. (2001) The Delis-Kaplan Executive Function System. San Antonio: Psychological Corporation. 2001); Auditory stroop test (Siu et al. (2008) *J Gerontol A Biol Sci Med Sci.* 63:1364-9)
d) Processing speed: Digit Symbol test (WAIS-R); Adjusting Paced Serial Addition Test (Royan et al. (2004) *Arch Clin Neuropsychol* 19:131-43);
e) Dual tasking (Bherer et al. (2008) *Exp Aging Res.* 34:188-219)
f) Long-term Memory: Rey Auditory Serial Addition Test (RAVLT), Hopkins Verbal Learning Test (HVLT; Rasmusson et al. (1995) *Arch Clin Neuropsychol.* 10:21-6); and
g) Generalization to daily life activities: Timed Instrumental Activities of Daily Living (TIADL; Smith et al. (2009) *JAm Geriatric Soc* 57: 594-603).

Example 3 Perceptual Assessments

Perceptual discrimination abilities are assessed at the pre- and post-training stage using an adaptive protocol of 'same'/'different' response judgments on two consecutively presented stimuli. Assessments are made with tones and sweeps. Participants are instructed to perform these perceptual assessment tasks under various conditions, such as (1) active attention to stimuli, (2) passive listening, and (3) active ignoring of stimuli; the latter two conditions primarily implemented to extract the neural signals associated with these conditions.

Example 4 Neural Assessment Measures

Neurophysiological measures are attained using electroencephalographic (EEG) recordings. Participants undergo two separate neural assessment sessions pre- as well as post-training (or post-wait period in control group).

The first neural assessment carried out in this example is a version of the training task, made to be fully compatible with the EEG recording set-up. Participants undergo a first training block at the lab, using this EEG-compatible version of the training software while simultaneously undergoing EEG recordings. Stimulus evoked responses, referred to as event-related potentials (ERPs), to targets as well as non-target (distracter) stimuli, are acquired. The magnitudes and latencies of the neural responses to targets and distracters index the forms and power of top-down modulation during selective attention to the task. These modulatory impacts are subsequently compared to ERP recordings in a similar post-training or control period assessment. ERP component metrics in both temporal and spectral domains are fit to a multivariate linear regression model with predictor variables of the stimulus parameters and outcome factors of behavioral performance on the task. Mis-matched negativities and related suppression dynamics are also recorded. Experimental measures are evaluated for their relationship to independent tests of cognition using multiple regression analyses.

The second neural assessment is carried out to probe neural modulations on an un-trained working memory (WM) task (adapted from Chao and Knight (1997) *Cereb Cortex* 7:63-9; Clapp et al. (2009) *Cereb Cortex.* 20:859-72; and Clapp et al. (2010) *Neurobiol Aging*. February 6), to assay neural generalizations of the effects of training Participants are presented a to-be-remembered cue-item, followed by a 10 sec delay period, then a probe-item that is either identical to the originally cued stimulus or differs in stimulus distance, from the cue equivalent to or proportional to the participant's pre-determined perceptual discrimination threshold. Participants are instructed to determine whether or not the identity of the probe stimulus matches the cue. This task can be composed of several condition variants such as, (1) in which the delay period contains no stimuli and hence purely tracks target (cue) encoding and processing over time, (2) in which irrelevant to-be-ignored stimuli (i.e. distracters) are inserted in the delay period assaying the intrusion of distracters on target processing, (3) in which to-be-discriminated interrupters are inserted in the delay period assaying the influence of an interruptive secondary task on the primary target processing, and (4) a condition that serves as baseline of passively perceiving (listening to) the stimulus stream. Pre- and post-training or control period ERP recordings that are time-locked to cue presentation, distracters, and probe stimuli are acquired, and assessed in relation to alterations in working memory performance on this un-trained task. A variety of electrophysiological timing, dynamic change, post-excitatory suppression, and frequency analyzed EEG measures are also derived from this simple recording study. Performance and related neural benefits documented in this study should directly assess the completeness of neurological recovery of age-related cognitive deficits achieved by the training.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A computer-implemented method for improving an individual's ability to suppress irrelevant stimuli, the method being implemented using one or more processors and a non-transitory computer-readable medium comprising instructions stored thereon, which when executed by the one or more processors, cause the one or more processors to perform operations comprising:
   presenting to the individual via an output device multiple sets of stimuli, wherein:
      each of the multiple sets of stimuli comprises three or more stimuli,
      at least one set of the multiple sets of stimuli comprises a target stimulus and an irrelevant stimulus, the irrelevant stimulus differing in at least one property from the target stimulus,
      at least one set of the multiple sets of stimuli does not comprise the target stimulus, and
      prior to presentation of a set of stimuli comprising the target stimulus and an irrelevant stimulus for the first time to the individual, the individual has not been informed of the target stimulus or its properties;
   receiving an input electronically from the individual in response to the presentation of at least one set of the multiple sets of stimuli, wherein:
      the input requires a physical action by the individual, and
      an input in response to a set of stimuli comprising the target stimulus is a correct input; and
   executing instructions to generate an output to inform the individual as to whether the input is correct.

2. The computer-implemented method according to claim 1, comprising repeating:
   the presenting step,
   the receiving step, and
   the executing instructions to generate an output, as a cycle and repeating said cycle with a selected time interval between cycles.

3. The computer-implemented method according to claim 1, wherein each of the multiple sets of stimuli comprises three or more visual stimuli, wherein at least one set of the multiple sets of the visual stimuli comprises a target visual stimulus and an irrelevant visual stimulus, the irrelevant visual stimulus differing in at least one property from the target visual stimulus.

4. The computer-implemented method according to claim 3, wherein the irrelevant visual stimulus differs from the target visual stimulus in one or more of brightness, color, shape, size, texture, orientation, and motion.

5. The computer-implemented method according to claim 3, wherein each of the multiple sets of visual stimuli is presented to the individual for up to 2 seconds.

6. The computer-implemented method according to claim 1, wherein each of the multiple sets of stimuli comprises three or more auditory stimuli.

7. The computer-implemented method according to claim 6, wherein the target auditory stimulus differs from the irrelevant auditory stimulus in a characteristic selected from the group consisting of: frequency, loudness, timbre, and any combination thereof.

8. The computer-implemented method according to claim 1, wherein the one or more non-transitory computer-readable media further comprise instructions that cause the one or more processors to determine a difficulty in discerning the target stimulus, and increasing or decreasing the difficulty based on said input.

9. The computer-implemented method according to claim 1, wherein the one or more non-transitory computer-readable media further comprise instructions that cause the one or more processors to generate an output which is a reward in response to a correct input.

10. The computer-implemented method according to claim 1, wherein the one or more non-transitory computer-readable media further comprise instructions that cause the one or more processors to generate an output which is a penalty in response to an incorrect input.

11. A non-transitory computer-readable medium comprising instructions stored thereon, which when executed by the one or more processors, cause the one or more processors to perform operations comprising:
   presenting to the individual via an output device multiple sets of stimuli, wherein:
      each of the multiple sets of stimuli comprises three or more stimuli,
      at least one set of the multiple sets of stimuli comprises a target stimulus and an irrelevant stimulus, the irrelevant stimulus differing in at least one property from the target stimulus,
      at least one set of the multiple sets of stimuli does not comprise the target stimulus, and
      prior to presentation of a set of stimuli comprising the target stimulus and an irrelevant stimulus for the first time to the individual, the individual has not been informed of the target stimulus or its properties;
   receiving an input electronically from the individual in response to the presentation of at least one set of the multiple sets of stimuli, wherein:
      the input requires a physical action by the individual, and
      an input in response to a set of stimuli comprising the target stimulus is a correct input; and
   executing instructions to generate an output to inform the individual as to whether the input is correct.

12. The non-transitory computer-readable medium of claim 11, comprising repeating:
   the presenting step,
   the receiving step, and
   the executing instructions to generate an output, as a cycle and repeating said cycle with a selected time interval between cycles.

13. The non-transitory computer-readable medium of claim 11, wherein each of the multiple sets of stimuli comprises three or more visual stimuli, wherein at least one set of the multiple sets of the visual stimuli comprises a target visual stimulus and an irrelevant visual stimulus, the irrelevant visual stimulus differing in at least one property from the target visual stimulus.

14. The non-transitory computer-readable medium of claim 13, wherein the irrelevant visual stimulus differs from the target visual stimulus in one or more of brightness, color, shape, size, texture, orientation, and motion.

15. The non-transitory computer-readable medium of claim 13, wherein each of the multiple sets of stimuli is presented to the individual for up to 2 seconds.

16. The non-transitory computer-readable medium of claim 11, wherein each of the multiple sets of stimuli comprises three or more auditory stimuli.

17. The non-transitory computer-readable medium of claim 16, wherein the target auditory stimulus differs from the irrelevant auditory stimulus in a characteristic selected from the group consisting of: frequency, loudness, timbre, and any combination thereof.

18. The non-transitory computer-readable medium of claim 11, wherein the one or more non-transitory computer-readable media further comprise instructions that cause the one or more processors to determine a difficulty in discerning the target stimulus, and increasing or decreasing the difficulty based on said input.

19. The non-transitory computer-readable medium of claim 11, wherein the one or more non-transitory computer-readable media further comprise instructions that cause the one or more processors to generate an output which is a reward in response to a correct input and/or generate an output which is a penalty in response to an incorrect input.

20. A computer device comprising the non-transitory computer-readable medium of claim 11.

* * * * *